(12) United States Patent
Konofagou et al.

(10) Patent No.: US 6,494,834 B2
(45) Date of Patent: Dec. 17, 2002

(54) POWER SPECTRAL STRAIN ESTIMATORS IN ELASTOGRAPHY

(75) Inventors: Elisa Konofagou, Boston, MA (US); Jonathan Ophir, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 74 days.

(21) Appl. No.: 09/810,958

(22) Filed: Mar. 16, 2001

(65) Prior Publication Data

US 2002/0010399 A1 Jan. 24, 2002

Related U.S. Application Data

(60) Provisional application No. 60/190,718, filed on Mar. 17, 2000.

(51) Int. Cl.[7] .................................................. A61B 8/00
(52) U.S. Cl. ....................................... 600/438; 600/449
(58) Field of Search .................................. 600/437, 438, 600/459, 440–449, 587, 594, 595, 454, 561; 73/625, 626, 593, 606; 128/903

(56) References Cited

U.S. PATENT DOCUMENTS

| | | | |
|---|---|---|---|
| 4,836,026 A | * 6/1989 | P'an et al. ..................... | 73/606 |
| 5,178,147 A | * 1/1993 | Ophir et al. .................. | 600/437 |
| 5,293,870 A | * 3/1994 | Ophir et al. .................. | 600/437 |
| 5,474,070 A | 12/1995 | Ophir et al. | |
| 5,810,731 A | * 9/1998 | Sarvazyan et al. .......... | 600/438 |
| 5,836,894 A | * 11/1998 | Sarvazyan ................... | 600/561 |
| 5,922,018 A | * 7/1999 | Sarvazyan ................... | 600/587 |
| 6,068,597 A | 5/2000 | Lin | |

OTHER PUBLICATIONS

Alam, SK, Ophir, J., and Konofagou E.E., An adaptive strain estimator for elastography, *IEEE Trans. Ultrason. Ferroel. Freq. Cont.*, vol. 45(2), pp. 461–472, (1998).

Alam, SK, Ophir, J., and Varghese T. Elastographic axial resolution: An experimental study, *IEEE Trans. Ultrason. Ferroel. Freq. Cont.* (in press).

Bamber, C. J., and Bush, L. N., Freehand elasticity imaging using speckle decorrelation rate, *Acoust. Imag.*, Editors Tortoli, P., and Masotti, L., vol. 22, pp. 285–292, (1996).

Bendat, J. S., and Piersol, A. C., *Random data: Analysis and measurement*, $2^{nd}$ ed., John Wiley, New York, (1986).

Bertrand, M., Meunier, M., Doucet, M., and Ferland, G., Ultrasonic biomechanical strain gauge based on speckle tracking, *Proc. 1989 IEEE Ultrason. Symp.*, pp. 859–864, (1989).

Bilgen, M. and Insana, M.F. Deformation models and correlation analysis in elastography, J. Acoust. Soc. Am., vol. 99 3212–3224, (1996).

(List continued on next page.)

*Primary Examiner*—Marvin M. Lateef
*Assistant Examiner*—Ali M. Imam
(74) *Attorney, Agent, or Firm*—Duane Morris LLP

(57) ABSTRACT

Elastography can produce quality strain images in vitro and in vivo. Standard elastography uses a coherent cross-correlation technique to estimate tissue displacement and tissue strain using a subsequent gradient operator. While coherent estimation methods generally have the advantage of being highly accurate and precise, even relatively small undesired motions are likely to cause enough signal decorrelation to produce significant degradation of the elastogram. For elastography to become more universally practical in such applications as hand-held, intravascular and abdominal imaging, the limitations associated with coherent strain estimation methods that require tissue and system stability, must be overcome. In this paper, we propose the use of a spectral shift method that uses a centroid shift estimate to measure local strain directly. Furthermore, we also show theoretically that a spectral bandwidth method can also provide a direct strain estimation. We demonstrate that strain estimation using the spectral shift technique is moderately less precise but far more robust than the cross-correlation method. A theoretical analysis as well as simulations and experimental results are used to illustrate the properties associated with this method.

4 Claims, 8 Drawing Sheets-

OTHER PUBLICATIONS

Bilgen, M. and Insana, M.F. Error analysis in acoustic elastography: II Strain estimation and SNR analysis, J. Acoust. Soc. Am., vol. 101 1147–1154, (1997).

Bracewell, R.N., *The Fourier Transform and its Applications*, 2nd ed, McGraw Hill, (1978).

Céspedes, E. I., Elastography: Imaging of Biological Tissue Elasticity, *Ph.D. Dissertation* University of Houston, (1993).

Céspedes, I., Ophir, J., Ponnekanti, H., Maklad, N., Elastography: elasticity imaging using ultrasound with application to muscle and breast in vivo, *Ultrasonic Imaging* 15, 73–88, (1993).

DeKorte, C. L., Céspedes, E.I., Van der Steen, A. F. W., and Lancee, C. T., Intravascular elasticity imaging using ultrasound: feasibility studies in phantoms, *Ultrasound Med. Biol.* vol. 23, No. 5, pp. 735–746, (1997).

Fellingham, L.L., and Sommer, P.G., Ultrasonic characterization of tissue structure in the in vivo human liver and spleen, *IEEE Trans. Sonics Ultrason. SU–31*, 418–428, (1984).

Flax, S. W., Pelc, N.J., Glover, G.H., Gutman, F.D. and Mclachlan, M. Spectral characterization and attenuation measurements in ultrasound, *Ultrasonic Imaging* vol. 5, pp. 95–116, (1983).

Fink, M., Hottier, F. and Cardoso, J.F. Ultrasonic signal processing for in vivo attenuation measurement: short time Fourier analysis, Ultrasonic imaging 5, pp. 117–135, (1983).

Garra, B. S., Céspedes, E.I., Ophir, J., Spratt R. S., Zuurbier R. A., Magnant, C. M., and Pennanen, M. F., Elastography of breast lesions: Initial clinical results, *Radiology*, vol. 202, pp. 79–86, (1997).

Gao, L., Parker K. J., Lerner, R. M., and Levinson, S. F., Imaging of the elastic properties of tissue– A review, *Ultrasound Med. Biol.*, vol. 22, No. 8, pp. 959–977, (1996).

Gerzberg L. and Meindl, J.D., Power–spectrum centroid detection for Doppler systems applications, *Ultrasonic Imaging*, vol. 2, pp. 232–261, (1980).

Hall T. J., Bilgen M., Insana M.F., and Krouskop, T.A., Phantom materials for elastography, *IEEE Trans. Ultrason. Ferroel. Freq. Cont.*, 44(6), 1355–1365, (1997).

Insana, M.F., Wagner, R.F., Garra, B.S, Brown, D.G., and Shawker, T.H., Analysis of ultrasound image texture via generalized Rician statistics, *Opt. Eng.* 25(6), 743–748 (1986).

Insana, M.F., Wagner R.F., Brown, D.G. and Hall, T.J., Describing small–scale structure in random media using pulse–echo ultrasound, J. Acous. Soc. Am. 87, 179–192, (1990).

Jensen, J.A., *Estimation of blood velocities using ultrasound*, Cambridge University Press, (1996).

Kallel, F., and Ophir, J., Three–dimensional tissue motion and image noise in elastography, *IEEE Trans. Ultrason., Ferroelec, Freq. Contr.*, vol. 44 (8), pp. 1286–1296, (1997a).

Kallel, F.; Ophir, J. A least squares estimator for elastography. Ultrasonic Imaging 19: 195–208; (1997b).

Konofagou, E.E, Ophir, J., Kallel, F. and Varghese, T. Elastographic dynamic range expansion using variable applied strains, *Ultrasonic Imaging*, vol. 19 (2) 145–166, (1997a).

Konofagou, EE, Varghese, T and Ophir, J., Variable compressions with RF and baseband processing for dynamic range expansion of elastograms, *Japan. J. Medical Ultrasonics*, vol. 24(5), pp. 753–760, (1997b).

Konofagou, E.E. and Ophir, J. A new elastographic method for estimation and imaging of lateral displacements, lateral strains, corrected axial strains and Poisson's ratios in tissues, *Ultras. Med. Biol.* 24(8):1183–1199, (1998).

Konofagou E., Kallel F. and Ophir J., Three–dimensional motion estimation in elastography, *1998 IEEE Symposium of Ultrasonics, Ferroelectrics and Frequency Control* in Sendai, Japan, Oct. 5–8, (1998).

Krouskop, T.A., Vinson, S., Goode, B., and Dougherty, D., A pulsed Doppler ultrasonic system for making noninvasive measurements of the mechanical properties of soft tissue, *J. Rehab. Res. and Dev.* 24, 1–8, (1987).

Kuc, R., Haghkerder, K., and O'Donnell, M., Presence of cepstral peaks in random reflected ultrasound signal, *Ultrasonic Imaging*, vol. 8, pp. 196–212, (1986).

Landini, L., and Verrazzani, L., Spectral characterization of tissue microstructure by ultrasound: A stochastic approach, *IEEE Trans. Ultrason. Ferroel. Freq. Cont.*, vol. 37, pp. 448–456 (1990).

Lerner, R. M., Huang, S. R. and Parker, K. J. "Sonoelasticity" images derived from ultrasound signals in mechanically vibrated tissues, *Ultrasound Med. Biol* 16, 231–239, (1990).

Lizzi, F. L., Ostromogilsky, M., Feleppa, E.J., Rorke, M.C. and Yaremko, M.M. Relationship of ultrasonic spectral parameters to features of tissue microstructure, IEEE Trans. Ultrason. Ferroel. and Freq. Control, vol. UFFC–33, No. 3, (1987).

Newhouse, V.L. and Amir, I. Time Dilation and Inversion Properties and the Output Spectrum of Pulsed Doppler Flowmeters, IEEE Trans on Sonics and Ultrasonics, vol. 30(3), pp. 174–179, 1983.

Ophir, J., Céspedes, E. I., Ponnekanti, H., Yazdi, Y., and Li, X., Elastography: a quantitative method for imaging the elasticity of biological tissues, *Ultrasonic Imaging*, vol. 13, pp. 111–134, (1991).

Ophir, J., Céspedes, I., Garra, B., Ponnekanti, H., Huang, Y., Maklad, N., Elastography: ultrasonic imaging of tissue strain and elastic modulus in vivo, *European Journal of Ultrasound*, vol. 3, pp. 49–70 (1996).

Ophir, J., Kallel, F., Varghese, T., Bertrand, M., Céspedes, I., and Ponnekanti, H., Elastography: A systems approach, The International Journal of Imaging Systems and Technology, John Wiley & Sons, Inc, vol. 8, pp. 89–103, (1997).

Parker, K. J., Huang, S. R., Musulin, R. A. and Lerner, R. M., Tissue response to mechanical vibrations for Sonoelasticity Imaging, *Ultrasound Med. Biol.*, vol. 16, pp. 241–246 (1990).

Shapo, B. M., Crowe, J. R., Skovoroda, A. R., Eberle, M. J., Cohn, N. A., and O'Donnell, M., Displacement and strain imaging of coronary arteries with intraluminal ultrasound, *IEEE Trans. Ultrason. Ferroel. Freq. Cont. vol. 43*, No. 2, pp. 234–246 (1996).

Soualmi, L., and Bertrand M., Endovascular elastography: Forward problem, (Abstract) $21^{st}$ International Symposium on Ultrasonic Imaging and Tissue Characterization, Jun. 3–5, (1996).

Talhami, H.E., Wilson, L. S., and Neale, M.L., Spectral tissue strain: A new technique for imaging tissue strain using intravascular ultrasound, *Ultrasound Med. Biol.* vol. 20, No. 8, pp. 759–772, (1994).

Varghese, T., and Donohue, K.D., Characterization of tissue microstructure scatterer distribution with spectral correlation, *Ultrasonic Imaging*, vol. 15, pp. 238–254, (1993).

Varghese, T., and Donohue, K.D., Mean scatterer spacing estimates with spectral correlation, Journal of the Acoustic Society of America, 96, 3504–3515, (1994).

Varghese, T., and Donohue, K.D., Estimating mean scatterer spacing estimates with the frequency–smoothed spectral autocorrelation function, *IEEE Trans. Ultrason. Ferroel. Freq. Cont.*. vol. 42 (3), pp. 451–463, (1995).

Varghese, T., *Spectral Redundancy in Tissue Characterization*, Ph.D. Dissertation, University of Kentucky, Mar. (1995).

Varghese, T., and Ophir, J., Estimating tissue strain from signal decorrelation using the correlation coefficient, *Ultrasound Med. Biol.*, vol. 22 (9), pp. 1249–1254, (1996).

Varghese, T., and Ophir, J., A theoretical framework for performance characterization of elastography : The Strain Filter, *IEEE Trans. Ultrason. Ferroel. Freq. Cont.*, vol. 44, No. 1, pp. 164–172, (1997).

Varghese, T., Bilgen, M., and Ophir, J., Multiresolution imaging in elastography, *IEEE Trans. Ultrason. Ferroel. Freq. Cont.*, vol. 45 (1), pp. 65–75, (1998).

Varghese, T., and Ophir, J., Characterization of elastographic noise using the envelope of echo signals, *Ultrasound Med. Biol.*, vol. 24 (4), pp. 543–555, (1998a).

Varghese, T and Ophir, J., A method for the experimental characterization of the noise performance of elastographic systems, (submitted) *Ultrasonic Imaging*, (1998b).

Varghese T., Konofagou E., Ophir J. and Alam S. K., Coherent vs. Incoherent Strain Estimation in Elastography, *AIUM conference*, San Antonio, Texas, Mar. 14–17, (1999).

Yamakoshi, Y., Sato, J., and Sato, T., Ultrasonic imaging of internal vibration of soft tissue under forced vibration, *IEEE Trans. Ultrason. Ferroel. Freq. Cont.*, vol. 37, No. 2, pp. 45–53, (1990).

Wagner, R.F.; Smith, S.W.; Sandrik, J.M. Lopez, H. Statistics of Speckle in Ultrasound B–Scans. IEEE Trans. on Son. and Ultras. 30, No. 3: 156–163; 1983.

Wagner, R.F., Insana, M.F., and Brown, D.G., Unified approach to the detection and classification of speckle texture in diagnostic ultrasound, *Opt. Eng.* 25(6), 738–742 (1986).

Wilson L. S., and Robinson D. E., Ultrasonic measurement of small displacements and deformations of tissue, *Ultrasonic Imag.*, vol. 4, pp. 71–82, (1982).

Zar, J.H. Biostatistical Analysis, $2^{nd}$ edition, Prentice Hall, 1984.

Bahr, R.K., Bucklew, J.A., and Flax, S.W., Optimal center frequency estimation for back–scattered ultrasound pulses, *IEEE Trans. Son. Ultrason.*, vol. 32 (6), pp. 809–814, (1985).

* cited by examiner

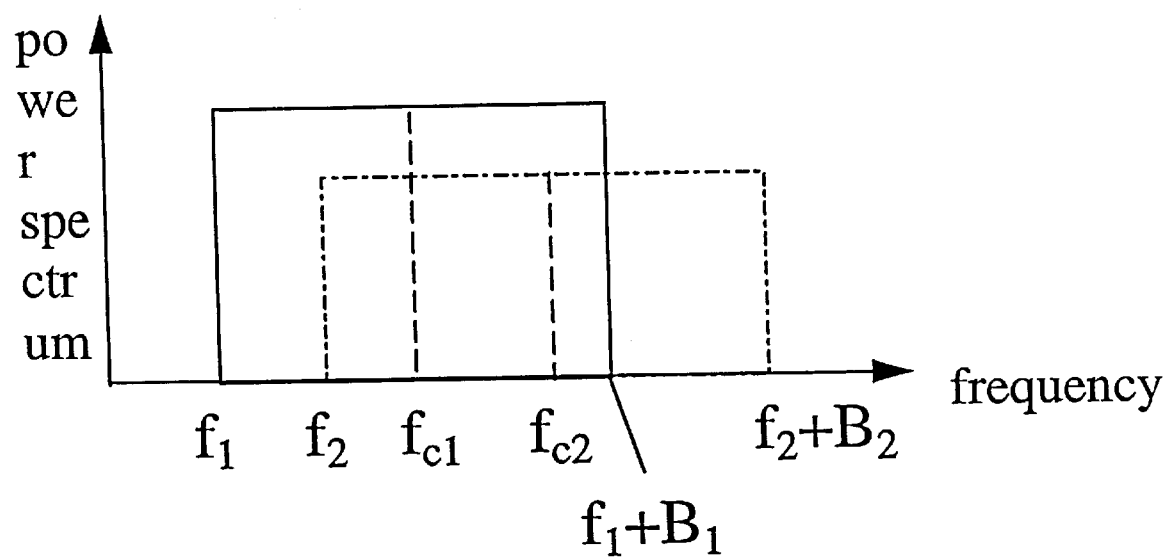
Figure B1

POWER SPECTRAL STRAIN ESTIMATORS IN ELASTOGRAPHY

This application claims the benefit of U.S. Provisional Application No. 60/190,718, filed on Mar. 17, 2000.

BACKGROUND OF THE INVENTION

1. Field of the Invention

The present invention relates to a method of measuring strain in a target body, using the transmission, reception, processing and normalization of ultrasound signals.

2. Description of the Prior Art

Imaging of elastic parameters of soft tissue has developed into a new tool for diagnosis of disease. Current estimators of tissue motion, include a time-domain cross-correlation based speckle tracking algorithm, and a Fourier based speckle phase-tracking technique. These techniques are coherent estimation techniques, i.e., these methods are sensitive to phase variations. The coherent estimation techniques generally have the advantage of being highly precise. Strain Filter (SF) analysis has shown, however, that they are not very robust in the presence of even a small amount of decorrelation between the pre- and post-compression signals. The term 'robustness' has been used in statistical analysis to denote the good performance of statistical tests, i.e., the homogeneity of the variance calculation, even if the data deviates from theoretical requirements. By equivalence in elastography, "robustness' denotes the consistently good performance of the estimator even at high decorrelation noise, i.e., keeping the variance of estimation at a relatively constant and low level at a large range of noise levels.

The term "decorrelation" as used herein, is defined as the loss of full correlation between the pre- and postcompressed windowed signal segments. Therefore, decorrelation may be encountered due to many sources, such as intrawindow axial motion undesired lateral or elevational motion, jitter (i.e., any cause of misregistration between the pre- and post-compressed A-line segments), unstable mechanical setup, etc. The main idea in this study is to introduce a new estimator that is more immune to decorrelation compared to other estimators.

SUMMARY OF THE INVENTION

The tissue strain estimator is a spectral estimator that estimates strain directly. Since the proposed estimator uses the power spectrum, it is incoherent, i.e., it does not use the phase of the signal. Previously reported incoherent methods include optical flow speckle tracking, envelope cross-correlation, and spectral chirp z-transform techniques. Generally, incoherent methods may be less precise but significantly more robust. For example, we have demonstrated this property for the case of time-delay estimation using the envelope of echo-signals. This may be a significant advantage where elastography is to be practiced in situations involving (1) undesired scanning motion, such as the case of using an unstable handheld transducer and/or (2) undesired tissue motion, such as abdominal or intravascular elastography. This property of the estimator is demonstrated later in this paper in the simulation results section through testing of its immunity to noise caused by jitter.

The main idea behind a spectral strain approach is based on the Fourier scaling property, which implies that a compression or expansion of the time-domain signal should lead to an expansion or compression of its power spectrum, respectively. One of the most well known and thoroughly studied spectral motion effects is the Doppler shift, which typically links the frequency shift to the scatterer velocity between emissions. Velocities towards the transducer result in a positive frequency shift, while the opposite is true for scatterers that move away from the transducer. However, since the scatterers within a given resolution length do not move at the same velocities, a spectrum of Doppler frequencies is observed. Therefore, initially in ultrasound, the methods of velocity estimation for the measurement of blood flow mainly operated in the frequency domain, otherwise known as spectrum analysis techniques and measured the mean velocity of scatterers across the vessel lumen (indicative of the volumetric flow rate) by estimating the mean frequency of the power spectrum. Despite the success of these techniques even in in vivo vessels, detection of the Doppler frequency shift, which is typically on the order of 1 kHz, is not possible for pulsed instruments, since the downshift in frequency due to attenuation (on the order of 10–100 kHz) is expected to dominate over the Doppler shift. Since in elastography the pre- and postcompressed segments are approximately identical depths, the attenuation effect on the two spectra is assumed to be identical and cancelled out when the two spectra are compared.

Strain estimation using spectral methods depends on the subsequent change in the scatterer statistics. Spectral methods typically link one or more signal parameters to the change in mean scatterer spacing. One prior art relates the relative change in the mean scatterer spacing to the strain incurred during a cardiac cycle. This method assumes the presence of underlying scatterer periodicities. Despite the fact that this has also been demonstrated to work in in vivo intravascular applications, the main assumptions of regular spacing or periodicities may not hold for most tissues. In contrast, as shown in the theory section, the spectral methods mentioned in this paper make no assumptions regarding the composition of the tissue scatterers.

Typically in elastography time-domain techniques are used that involve the computation of the time-delay to estimate the displacement following an applied compression, and the estimation of strain by applying gradient operations on the previously obtained time-delay estimates. As mentioned earlier, an important advantage associated with these spectral methods as well as other estimators, such as the adaptive stretching estimator, is that they can be used to estimate strain directly; i.e., without involving the use of noisy gradient operators. In the latter case, the gradient operation introduces additional amplification of the noise into the strain estimation process, thus degrading the strain estimates. Furthermore, similar to the adaptive stretching estimator, only one estimation window is needed, for both the magnitude and the sign of the strain to be estimated.

As shown later in the theory section, spectral estimators can be divided into two main groups: a) the spectral shift methods and b) the spectral bandwidth methods. Despite the fact that we develop expressions that show direct strain estimation in both cases, in this paper we focus primarily on a spectral shift method; we estimate the relative shift in the spectral centroid caused by compressive or tensile tissue strain. Therefore, throughout this paper this new estimator is referred to as the "centroid strain estimator", "centroid estimator" or "centroid method". Current investigations that deal with the development of alternative shift estimators as well as bandwidth estimators will not be reported in this study.

The spectral centroid has been widely used in estimating the Doppler shift, attenuation and backscattering. The theory underlying the use of centroid strain estimators is presented in the next section. One-dimensional (1-D), instead of two-dimensional (2-D), motion simulations are used in order to more accurately study the performance of the estimator, i.e., independent of the effect of signal decorrelation in two dimensions that complicates the measurements. Simulation results in 1-D illustrate the insensitivity of the centroid strain estimator to signal decorrelation effects. It is important to note that, as mentioned earlier, decorrelation can be due to several sources. For the purpose of this paper, we consider solely the axial decorrelation effect in this 1-D model. We, thus, assume that the robustness demonstrated by the spectral estimator vis-à-vis this effect is a more general property that can be further applied at other decorrelation scenarios. For example, it is shown in the results section how the spectral method is indeed more immune to jitter, another source of decorrelation. The elastograms obtained using these simulations as well as phantom experiments illustrate the robustness of the spectral centroid strain estimator. The properties of the new estimator are discussed and summarized in the Conclusion section.

In this section, we show analytically that for Gaussian echo spectra, the relative spectral shift is a direct measure of tissue strain. We also show the relative bandwidth variation can also be used as a direct strain estimator.

Signal and noise model.

The pre- and post-compression echo signals are given as follows:

$$r_1(z) = h(z)*e(z) + n_1(z) \quad (1)$$

$$r_2(z) = h(z)*e(az) + n_2(z) \quad (2)$$

where z is a spatial variable, $r_1(z)$ and $r_1(z)$ are the received RF signals before and after compression, respectively, h(z) is the impulse response of the ultrasound system or point-spread function (PSF), e(z) is the scattering function, $n_1(z)$ and $n_2(z)$ are independent zero-mean white noise sources and α is the compression coefficient (or, strain factor) linked to strain s through $$a = \frac{1}{1-s} \cong 1 + s \quad (3)$$

The approximation holds for s<<1, where the strain s for a one-dimensional homogeneous target is typically defined in mechanics by $$s = \frac{L_0 - L}{L_0} \quad (4)$$

where $L_0$ and $L$ are the pre- and postcompressed axial dimensions of the target. From Eq. (4) the reader should note that positive strain denotes compression (and a>1) while negative strain denotes tension (and a<1). The reader should note that throughout this paper the subscripts $_1$ and $_2$ denote pre- and postcompression parameters, respectively.

Assuming that h(z) and e(z) in Eqs. (1) and (2) can be described by their autocorrelation functions that may be modeled by modulated Gaussian functions, we obtain $$h(z) = \frac{1}{\sqrt{2\pi} L_h} \exp(-z^2/2L_h^2) \sin(k_h z) \quad (5)$$

and

-continued $$e(z) = \frac{1}{\sqrt{2\pi} L_e} \exp(-z^2/2L_e^2) \cos(k_e z) \quad (6)$$

where $L_h$ and $L_e$ are the resolution lengths of the PSF and of the scattering function, respectively, $k_h$ is the central spatial frequency of the PSF, and $k_e$ is the central spatial frequency of the scattering function.

The one-sided power spectra of the pre- and post-compression RF signals (positive frequencies) are given respectively by $$R_1(k) = \frac{1}{4}\exp\left(-\frac{1}{2}[(k-k_h)^2 L_h^2 + (k-k_e)^2 L_e^2]\right) + N_1(k) \quad (7)$$

$$R_2(k) = \frac{1}{4a}\exp\left(-\frac{1}{2}\left[(k-k_h)^2 L_h^2 + (k-ak_e)^2 \frac{L_e^2}{a^2}\right]\right) + N_2(k) \quad (8)$$

where $N_1(k)$ and $N_2(k)$ are independent power spectra of zero-mean white noise processes, i.e., $$\langle N_1(k) \rangle = \langle N_2(k) \rangle = 0.$$

A brief observation of Eqs. (7) and (8) reveals the centroid shift in the scattering spectrum resulting from the compression. In other words, if $f^{e1}$ and $f^{e2}$ are the center frequencies of the scattering spectrum before and after compression, respectively, and assuming that the speed of sound in the tissue c remains constant, from Eqs. (7) and (8) we have $$f_{e2} - f_{e1} = \frac{c}{2\pi}(ak_e - k_e) \quad (9)$$

$$= (a-1)f_{e1},$$

or, from Eq. (3)

$$\frac{f_{e2} - f_{e1}}{f_{e1}} \cong s \quad (10)$$

So, the relative centroid shift in the scattering function spectrum constitutes a direct strain estimator. A similar result is found later (Eq. 16) using the spectrum of the received signal. In the section below, we use Eq. (10) as a guide in the formulation of the new estimator.

Effect of strain on the spectrum of the received signal

The centroid of the power spectrum of the received signal is defined as follows $$f_c = \frac{c}{2\pi} \frac{\int_{-\infty}^{\infty} k R_1(k) dk}{\int_{-\infty}^{\infty} R_1(k) dk}. \quad (11)$$

The centroid estimate for the precompression power spectrum is given by:

$$f_{e1} = \frac{c}{2\pi} \frac{k_h L_h^2 + k_e L_e^2}{L_h^2 + L_e^2} \quad (12)$$

In a similar manner we can derive the expression for the centroid of the post-compression power spectrum by replacing $k_e$, and $L_e$, in Eq. (9) by their corresponding parameters in the post-compression power spectrum, i.e., $ak_e$ and $$\frac{L_e}{a}$$

(as indicated from Eq. 7) to obtain:

$$f_{c2} = \frac{c}{2\pi} \frac{k_h L_h^2 + k_e \frac{L_e^2}{a}}{L_h^2 + \frac{L_e^2}{a^2}} \qquad (13)$$

Note that the PSF parameters remain unchanged. Since both centroids depend on the center frequencies and bandwidths of the scattering function and the PSF and by consulting Eq. (10), we normalize this effect by using the following ratio as a candidate strain estimator:

$$\frac{f_{c2} - f_{c1}}{f_{c1}} = \frac{\frac{k_h a^2 L_h^2 + a k_e L_e^2}{a^2 L_h^2 + L_e^2} - \frac{k_h L_h^2 + k_e L_e^2}{L_h^2 + L_e^2}}{\frac{k_h L_h^2 + k_e L_e^2}{L_h^2 + L_e^2}} \qquad (14)$$

The parameters $L_e$ and $L_h$ are related to $B_e$ and $B_h$, the equivalent noise spectral bandwidths for the scattering and PSF spectra, through $$B_h = \frac{1}{2\sqrt{\pi} L_h} \text{ and } B_e = \frac{1}{2\sqrt{\pi} L_e},$$

respectively.

However, the PSF bandwidth is typically much smaller than the bandwidth of the scattering function, i.e., $B_e >> B_h$; thereby, $L_e << L_h$ and, therefore, $a^2 L_h^2 >> L_e^2$. After cancellation of common terms in the numerator and denominator of Eq. (14), we obtain $$\frac{f_{c2} - f_{c1}}{f_{c1}} \cong \frac{(a-1)\frac{k_e L_e^2}{L_h^2 + L_e^2}}{\frac{k_h L_h^2 + k_e L_e^2}{L_h^2 + L_e^2}} \qquad (15)$$

$$= \frac{(a-1)}{\frac{k_h L_h^2}{k_e L_e^2} + 1}$$

or, from the small strain approximation case of Eq. (3) (i.e., in mathematical terms, for strains less than 10%), $$\frac{f_{c2} - f_{c1}}{f_{c1}} \cong As \qquad (16)$$

where A is given by $$A = \frac{1}{\frac{k_h L_h^2}{k_e L_e^2} + 1} \qquad (17)$$

or, $$A \cong \frac{k_e B_h^2}{k_h B_e^2} \qquad (18)$$

Inspection of Eq. (16) leads to the following interesting observations:

The relative spectral centroid shift can be used as a direct strain estimator. We can also observe a direct analogy between the classic definition of strain (Eq. (4)) and the estimator of Eq. (16), which establishes this method as a simple and straight-forward way of estimating the strain.

When the strain is positive (or, compressive), a frequency upshift occurs, i.e., $f_{c2} - f_{c1} > 0$. Conversely, a tensile (or, negative) strain results in a frequency downshift, i.e., $f_{c2} - f_{c1} < 0$. Therefore, the estimator of Eq. (16) provides directly not only the magnitude of the strain but also its sign.

Since constant A is independent of the strain, it will introduce a uniform bias on the resulting elastogram. This should not affect the resulting elastogram, since the latter depicts relative values of strain. The reader should note that the effect of local bandwidth variations is ignored.

The scattering spectrum must be a bandpass and band-limited spectrum in order to estimate the strain using the centroid estimator. Otherwise, if $B_e$ is infinite and/or if $k_e$ is zero, constant A in Eq. (16) will always be zero regardless the strain.

For relatively larger strains, using the more general form of Eq. (3), Eq. (16) becomes $$\frac{f_{c2} - f_{c1}}{f_{c1}} \cong A \frac{s}{1-s}$$

or, by solving for the strain, $$s \cong \frac{f_{c2} - f_{c1}}{(A-1)f_{c1} + f_{c2}} \qquad (19)$$

which is a less straight-forward, but still a direct way of estimating higher strains.

Eq. (16) is reminiscent of the well-known Doppler effect, according to which the ratio of the centroid shift to the center frequency may provide a reliable measure of velocity. According to Eq. (16), in the case of strain, a similar effect also occurs. Also, among others have shown how in broadband Doppler the bandwidth of the resulting spectrum also changes with velocity and that the output RF Doppler spectrum is a frequency-shifted and compressed (or stretched) replica of the transmitted one. Similarly, in the case of strain measurement, that the following expression provides a direct estimation of strain:

$$\frac{B_2 - B_1}{B_1} \cong ks \qquad (20)$$

where and are the post- and precompression bandwidths, respectively and k is a constant. So, strain, like velocity, introduces these two coupled effects of centroid shift and bandwidth variation in the power spectrum. Spectral broadening (i.e., in the case of compression) or contraction (i.e., in the case of tension) can introduce a bias in the measurement. A general expression is derived, linking the centroids $f_{c1}$ and $f_{c2}$ (before and after compression, respectively), the pure frequency shift (i.e., in case the pre and postcompression spectra are identical, only centered at different frequencies separated by a shift), $\Delta f$, and a bias term $\beta$ denoting the spectral broadening (or, compression) due to strain s:

$$f_{c2}-f_{c1}=\Delta f+\beta(s) \tag{21}$$

where $$\beta(s)=B_2(s)-B_1 \tag{22}$$

In order to estimate the strain without the bias associated with spectral broadening, the following equation can be used that results from Eqs. (16), (20), (21) and (22):

$$\Delta f \cong A f_{c1} s - k B_1 s \tag{23}$$

and solving for strain, the unbiased estimator is given by $$s \cong \frac{\Delta f}{A f_{c_1} - k B_1} \tag{24}$$

However, Eq. (24) requires a bandwidth estimation and since the bandwidth estimator is not part of this study, we use Eq. (16) as the strain estimator and show a bias with simulations, which is partly due to the previously described bias due to spectral broadening.

DESCRIPTION OF THE DRAWINGS

FIG. 6 (ii) a–c are elastographs.

FIG. 6 (iii) a–c are elastographs.

Figure 1:
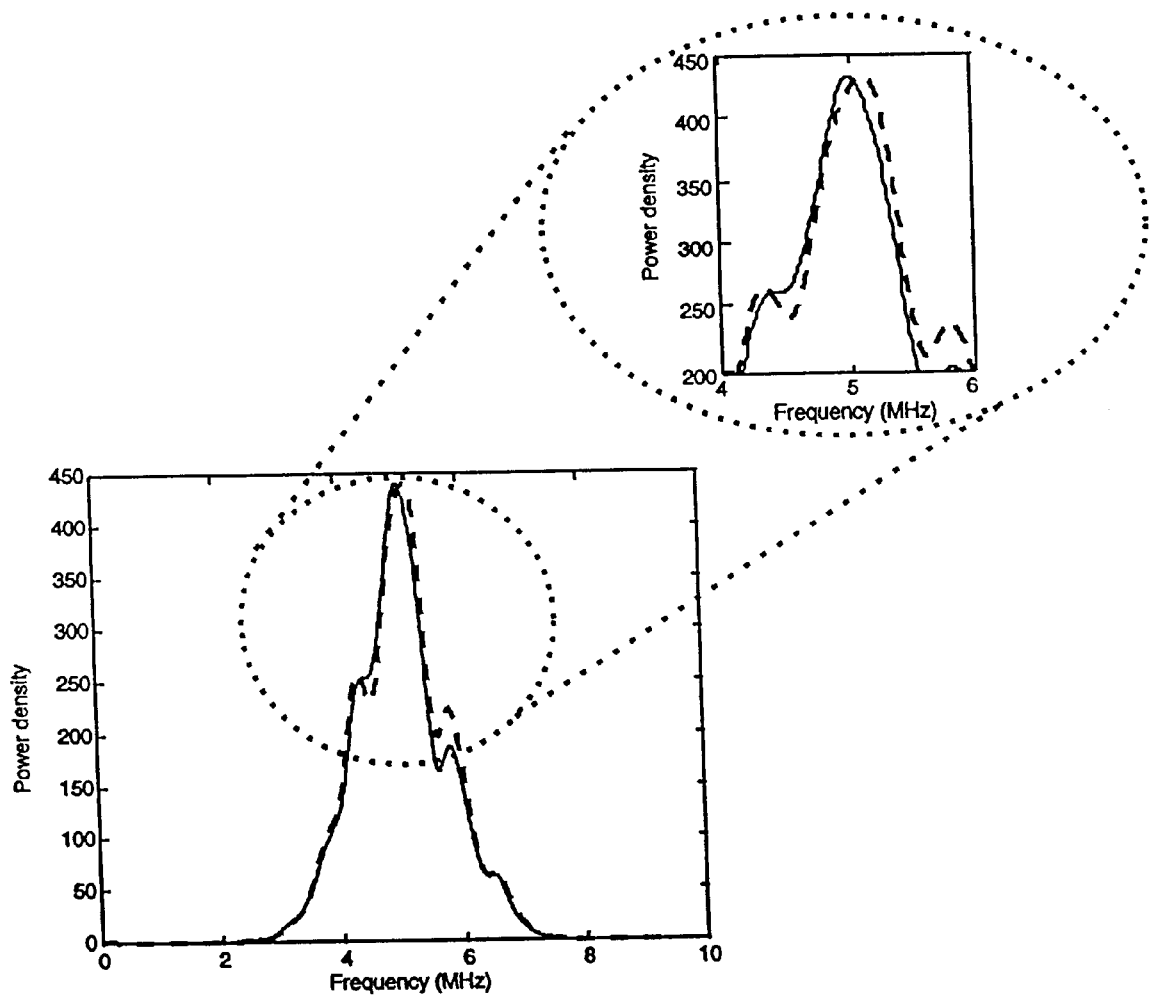
FIG. 1 is a graph of power density verses frequency.

FIG. B1 is a graph of power spectrum verses frequency.

DESCRIPTION OF THE PREFERRED EMBODIMENTS

Simulation results using a 1-D scattering model is used in this section to illustrate the performance of the centroid strain estimator. Strain estimation using the centroid is also compared to the standard cross-correlation based algorithm.

Monte-Carlo simulations in MATLAB (Mathworks, Inc., Natick, Mass., USA) are used to generate pre- and post-compression RF signals for a 30 mm target segment and sampled at 48 MHZ. The speed of sound in tissue was assumed-to be-constant at 1540 m/s. The PSF was simulated using a Gaussian modulated cosine pulse with a wave number=20.4 mm (5 MHZ center frequency, 50% bandwidth), and a 0.2138 mm standard deviation unless stated otherwise. The scattering function consisted of randomly distributed point scatterers following a uniform distribution with density of 40 scatterers/pulse-width in order to simulate Gaussian statistics. We assume that the uniformly distributed scatterers are of a sufficient number to generate an echo signal with circular Gaussian statistics. The PSF was convolved with the scattering function to obtain the pre-compression RF signal. The postcompression signals were generated after applying a uniform compression of the point scatterers, and convolving the compressed point scatterers with the original PSF.

Spectral strain estimation (following Eqs. 16 and 11) was performed using pre- and postcompressed power spectra of windowed RF signals. The signal length equaled 4 mm and the size of postcompression window was changed with strain in order to assure that the same tissue information was incorporated in both the pre- and postcompressed windows. The length of the data segment incurred the usual tradeoff in spectrum estimation. A larger window length improved the spectrum as long as the data was stationary. Moreover, it was recently shown that the overlap has a more significant impact on resolution than the window length. As a result, larger windows with high overlap can generally provide both a smoothing effect on the noise and high resolution for both the time-domain and spectral estimators. This effect, however, needs to be further investigated.

The power spectra calculation of the pre- and postcompressed RF segments was performed using a 25-point frequency smoothing window unless otherwise stated. The 25 point frequency smoothing window represent only 0.6% of the entire FFT and is a relative small window. Frequency smoothing is similar to using a moving-average window, however the averaging is performed on the complex spectrum to obtain an estimate of the power spectrum. Frequency smoothing allowed the use of a single pair of A-lines, similar to the strain estimation performed using the crosscorrelation-based strain estimator. We use a 1024 point chirp Z-Transform to compute the spectrum which would correspond to a 4096 point FFT (since we use only one half of the spectrum, and only the region with a sufficient signal). The mean and standard deviation of the strain estimates were obtained by processing pre- and postcompression A-lines with a total length of 30 mm. The corresponding $SNR_e$ (ratio of the mean of the estimated strain to its standard deviation) values were obtained using Monte Carlo simulations in MATLAB with 25 independent realizations for each strain value. The simulated Strain Filters were obtained by plotting the $SNR_e$ estimates for the whole range of the applied tissue strains. The Strain Filter typically addresses the limitations of the ultrasound system (such as time-bandwidth product, center frequency and sonographic SNR) as well as the signal processing algorithms used to process the signals through the introduction of constraints in the attainable elastographic SNR, resolution, sensitivity and strain dynamic range.

The robustness of the strain estimators was also evaluated by introducing jitter errors in the scatterer positions before generating the post-compression signals. The jitter in the scatterer positions followed a normal distribution that varied randomly from zero to the maximum value of the jitter introduced. For the larger jitter values the scatterers could move out of the window of estimation. The strain estimation accuracy and precision for the coherent estimators were expected to deteriorate under these conditions since they depend on the relative motion of the scatterers themselves with compression. However, the centroid estimator, being incoherent, was expected to show strain estimation with a reasonable $SNR_e$ even at high jitter levels.

Figure 2:
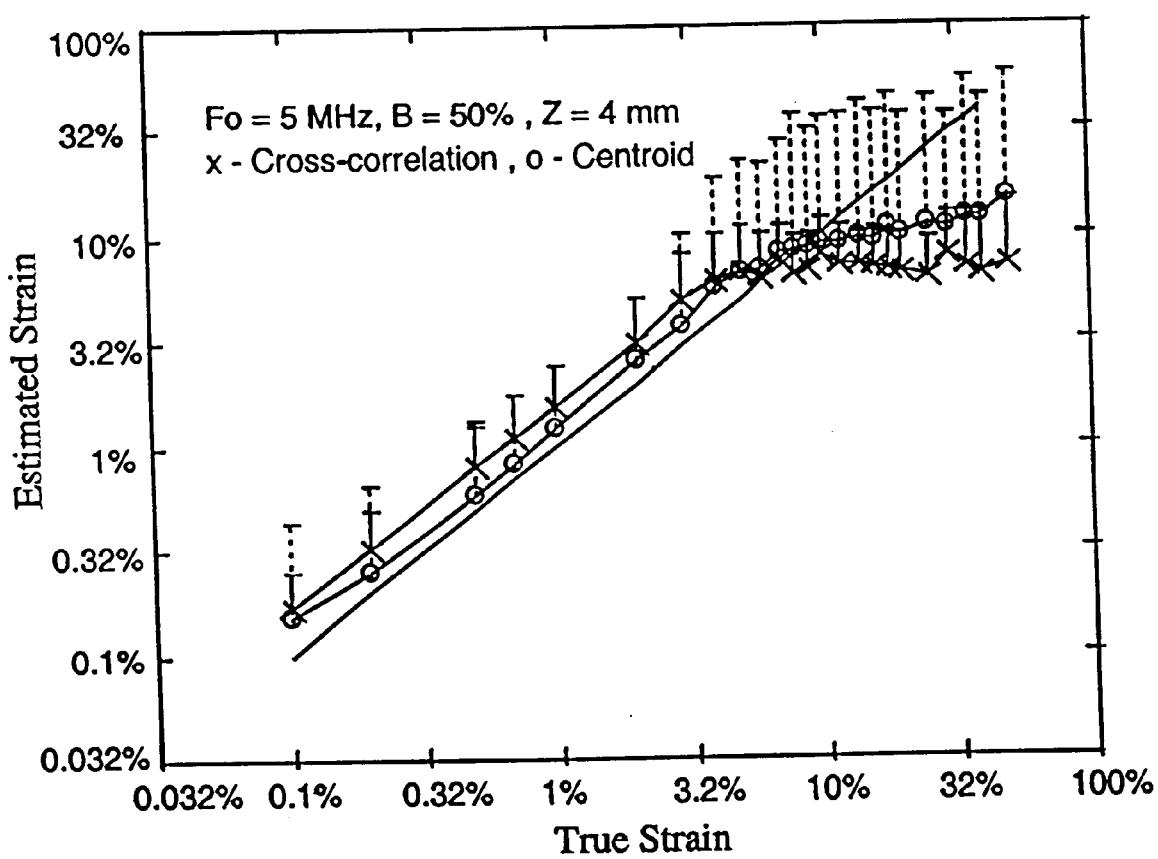
FIG. 2 is a graph of estimated strain verses true strain.

An example of the frequency shift on simulated spectra of entire A-lines (40 mm in length) is shown in FIG. 1 for the case of 1% applied strain. Comparison of the strain estimators using the coherent cross-correlation and centroid based algorithms are presented in FIGS. 2 and 3 for the 1-D simulations. The mean strain estimates and their standard deviation are presented in FIG. 2 and the respective simulated Strain Filters are presented in FIG. 3. The results in FIG. 2 illustrate that the strain estimates from both estimators follow the theoretical curve (straight solid line at 45 degrees) for strains less than 5%, where the cross-correlation strain estimator begins to level off, and at 8% where the centroid strain estimator crosses the theoretical curve. Both estimators are biased with a small overestimation of the strain seen for strains lower than 5%. For larger strains, the centroid estimator underestimates the actual strain values with a larger bias in the estimated strain value. This bias in the strain estimation for the centroid estimator is at least partly due to the bandwidth broadening, as discussed in the theory section. The bias in the cross-correlation based strain estimator is due to the errors associated with tissue compression that corrupt the time-delay estimates. These bias errors can be reduced by temporally stretching the post-compression data. Overall, when compared to the standard elastographic coherent estimator, the centroid strain estimator provides a biased but more robust strain estimate.

Figure 3:
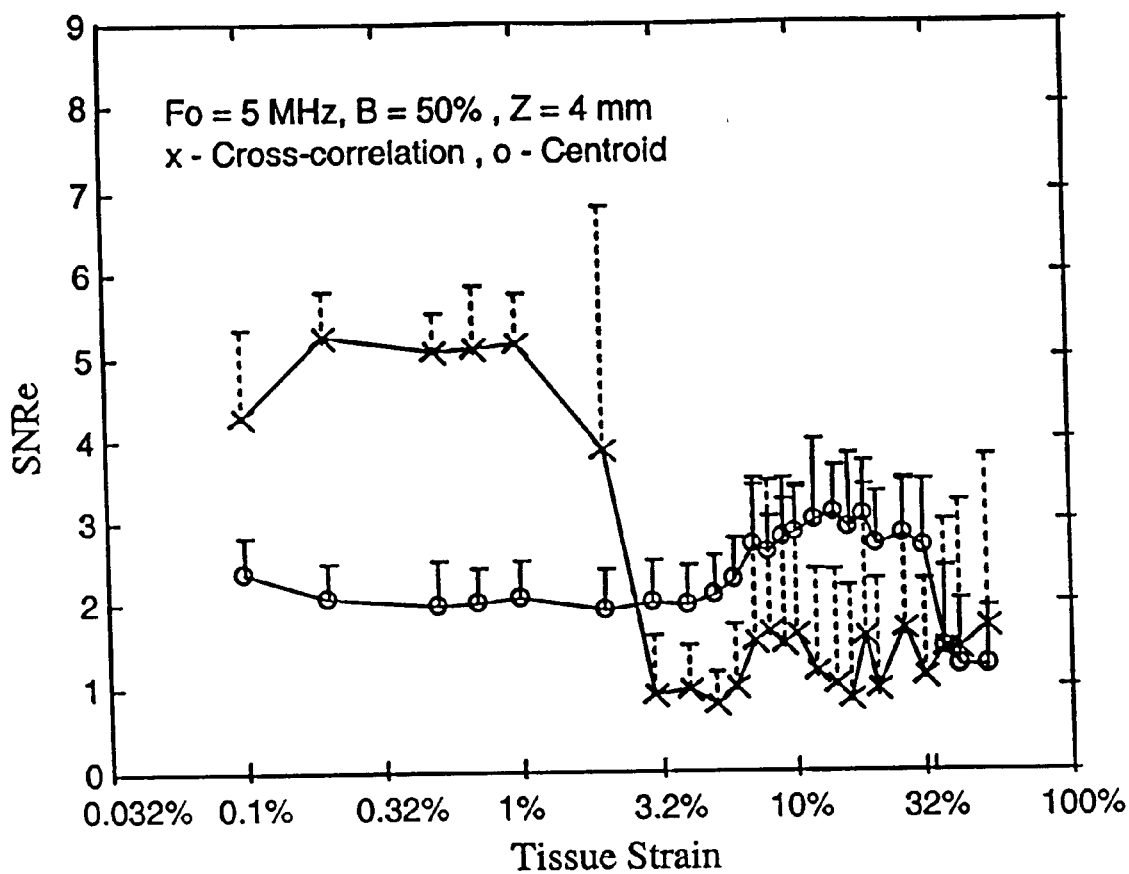
FIG. 3 is a graph of signal to noise ratio verses tissue strain.

In FIG. 3, the simulation Strain Filters for the two algorithms illustrate the noise performance of the estimators. Note that the coherent cross-correlation strain estimator provides accurate and precise strain estimates for strains less than 2%, since the variance increases rapidly beyond this strain value; however, for larger strains the performance deteriorates significantly. On the other hand, the centroid strain estimator, not being sensitive to phase, provides a robust strain estimate even at very large strains close to 30%. The SF for the centroid strain estimator indicates a reasonable $SNR_e$ for low tissue strains as well as an increase in the $SNR_e$ observed for larger strains where the cross-correlation strain estimator is limited by signal decorrelation errors. Due to its lower precision the centroid estimator works best at higher strains, where the shift is greater and therefore the signal-to-noise ratio (assuming the variance remains constant) increases, as shown in FIG. 3. The simulations therefore show the robustness of the spectral centroid strain estimator to large applied strains and increased jitter, errors that are most likely to be encountered in hand-held or intravascular or abdominal elastography.

Figure 4:
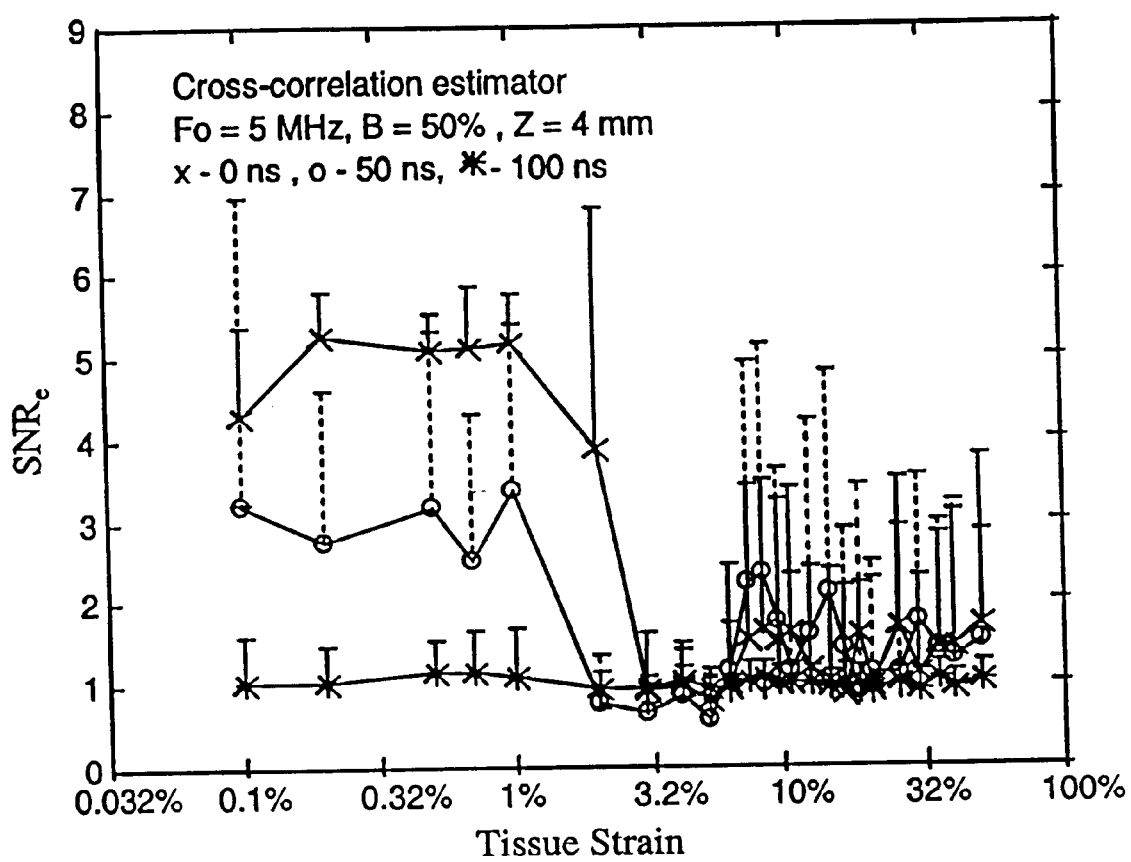
FIG. 4 is a graph of signal to noise ratio verses tissue strain.
Figure 5:
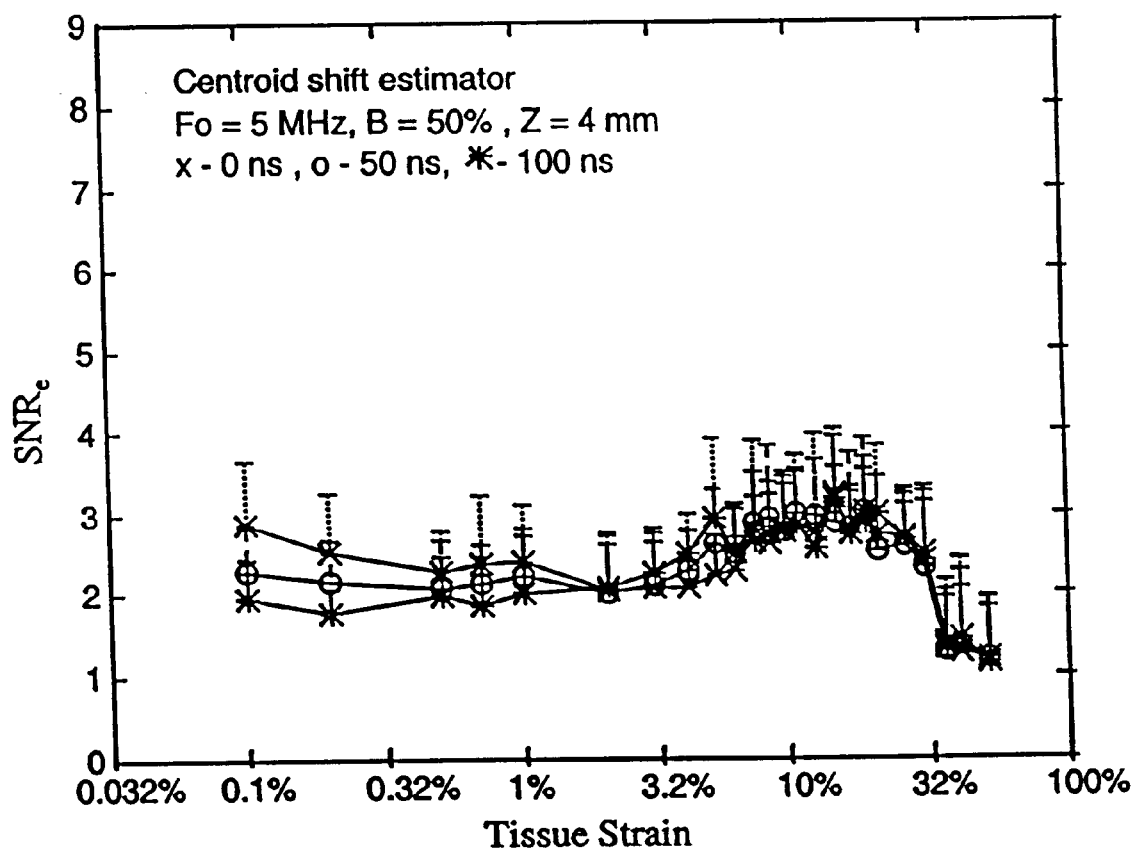
FIG. 5 is a graph of signal to noise ratio verses tissue strain.

Next, we investigated the sensitivity of the crosscorrelation and spectral strain estimator to variations in the scatterer positions caused due to axial jitter. The results are illustrated in FIGS. 4 and 5 for the cross-correlation and centroid strain estimators respectively. Note that the coherent crosscorrelation-based strain estimator is more susceptible to jitter than the centroid strain estimator. The noise performance of the cross-correlation estimator drops by about 50% with an increase in the maximum value of the jitter by 50 ns. However, in the case of the centroid strain estimator the noise performance remains at the same high level, even at jitter magnitudes of 100 ns. The simulations, therefore, show the robustness of the spectral centroid strain estimator to large applied strains and increased jitter, errors that are most likely to be encountered in hand held or intravascular or abdominal elastography. The two following sections compare elastograms obtained with these two estimators in the case of a 1-D finite-element simulation and an experimental phantom.

Elastograms using simulated data

After testing the properties of the new estimator in the previous section, elastograms were generated for a simulated single inclusion phantom under uniform compression. For the calculation of the displacements, we used a finite element analysis (FEA) commercial software (ALGOR, Inc., Pittsburgh, Pa., USA). The simulated totally compressible and isotropic phantom contained a single inclusion three times harder than the homogeneous background (background modulus=21 kPa). All nodes were constrained to move solely in the axial direction, thereby avoiding decorrelation in other directions. This motion model was therefore considered onedimensional. The scatterers were normally distributed. The ultrasonic parameters were as follows: center frequency 5 MHZ, 50% 6 dB bandwidth and 100 A-lines.

The strain estimation noise performance of the centroid estimator was compared to that of the standard elastographic crosscorrelation-based strain estimator without motion compensation, i.e., global stretching. As explained in the introduction, motion compensation was not used, since the noise to which the robustness of the two estimators is tested is precisely the one due to axial motion.

Figure 6:
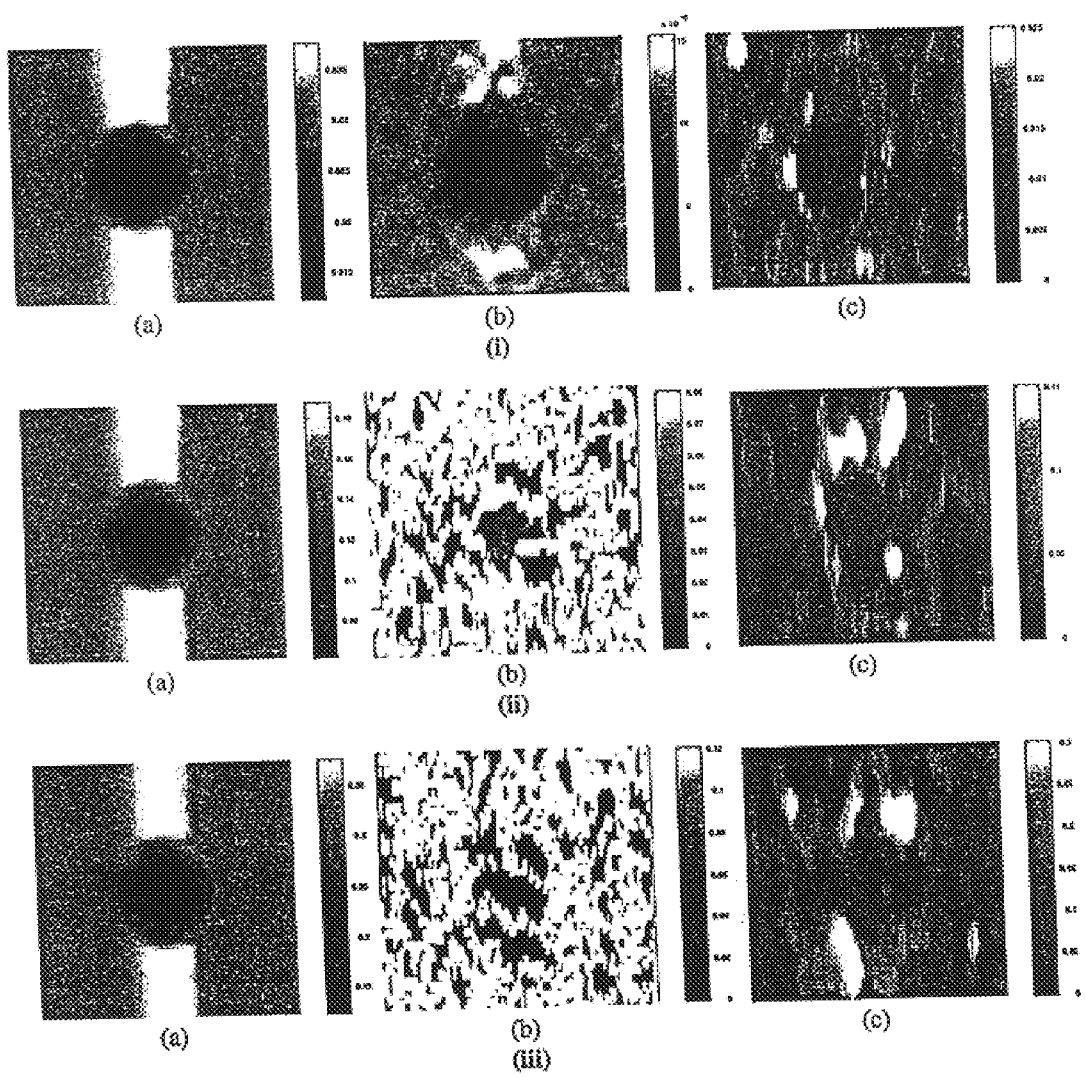
FIG. 6 (i) a–c are elastographs.

FIG. 6 presents the elastograms obtained using both these methods along with the ideal elastogram. (i.e., true strain image) for three different applied compressions. Note that at the low strain value of 1% (FIG. 6 (i)) the elastogram generated using the cross-correlation algorithm provides the closest correspondence to the ideal elastogram. On the other hand, for larger applied strains (5% and 10%, FIG. 6 (ii) & (iii)) the cross-correlation algorithm fails to accurately estimate tissue strain due to the increased signal decorrelation errors (FIG. 6b (ii & iii), respectively). In fact, at 5% applied compression part of the inclusion is still visible, being three times harder than the background and, thus, experiencing a much lower strain allowing it to be depicted with a good signal-to-noise ratio. On the other hand, the elastogram generated using the spectral centroid method at 5% and 10% compression (FIG. 6c (ii & iii), respectively) illustrates the robustness associated with the centroid method.

In the next section, we present elastograms obtained using an elastographic experimental phantom. The experimental results provide a complete 3-D situation where axial, lateral and elevational signal decorrelation are present, unlike the 1-D situation illustrated in this section.

Elastograms using experimental data

The ultrasound system used for taking the data was a Diasonics Spectra II real-time scanner (Diasonics Inc., Santa Clara, Calif.) operating with dynamic receive focusing and a single transmit focus centered at a depth of 3 cm. The transducer used was a 5 MHZ linear array (40 mm) with a 60% fractional bandwidth. The digitizer used is a 8-bit digitizer (LeCroy Corp., Spring Valley, N.Y.) with a sampling rate of 48 MHZ. The digitized data was collected from a 40×50 mm ROI consisting of 100 A-lines (starting at a depth of 5 mm under the transducer) centered around the transmit focus. The system also included a motion control system, and a compression device. A personal computer controlled the operation of the entire system.

A gelatin phantom[1] (90×90×90 $mm^3$) containing a cylindrical inclusion with a 20 mm diameter, positioned at the center of the phantom and three times stiffer than the background was used to compare the performance of the strain estimators. The phantom contains scatterers (graphite flakes) and was used to obtain RF scans before and after compression. A large compressor was used to simulate uniform stress conditions in the phantom. The phantom was lubricated on the top and bottom surfaces with corn-oil to simulate slip boundary conditions and was free on both lateral and elevational sides.

Figure 7:
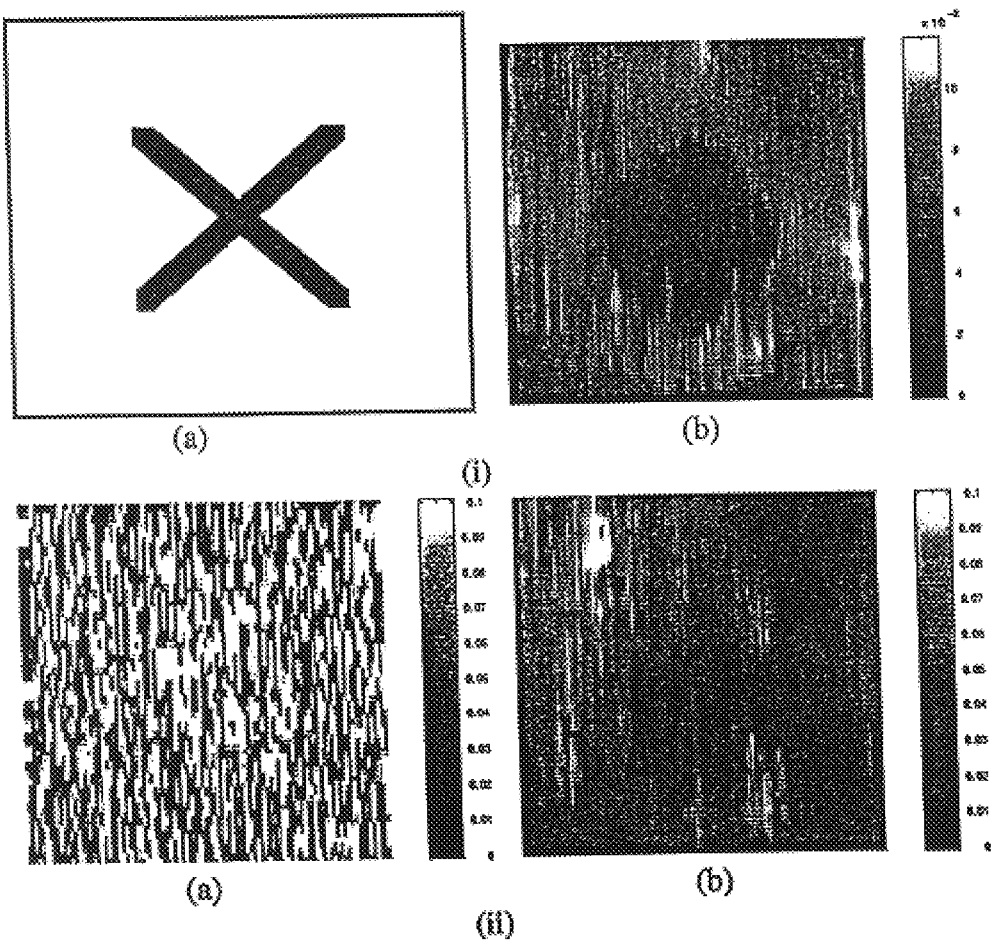
FIG. 7 comprises various elastographs.

Comparison of the estimation performance using coherent cross-correlation and centroid strain estimators is illustrated qualitatively using elastograms obtained at both low (0.5%) and high (3%) applied strains in FIG. 7. Note that coherent strain estimation provides the elastogram with the highest for the low compression of 0.5% (FIG. 7 (i)), when compared to the centroid method. However, for the large applied compression of 3% (FIG. 7 (ii)) the coherent strain estimator fails completely when compared to the spectral centroid method which produces a reasonable elastogram. In addition, averaging several elastograms obtained from independent pre- and post-compression data can be used to further improve the elastograms for the centroid method. However, averaging is not useful-for the coherent cross-correlation strain estimator in this case since the RF signals are completely decorrelated producing (FIG. 7a (ii)).

[1] The elastrographic phantom was supplied courtesy of Dr. Timothy Hall (Hall et al. 1997).

Two major differences can be observed between the 1-D simulation results and the experimental results: a) The mechanical artifacts for the I-D simulation elastograms are along the top and bottom axes of the inclusion, when compared to the more complicated artifacts observed for the 3-D case and b) the cross-correlation algorithm fails at relatively lower applied strains (3% instead of 5% or 10%) than in the simulation results due to lateral and elevational decorrelating motion involved. The centroid method yields similar results in both cases of low and high applied strains demonstrating its robustness in a 3-D scenario as well. These results are comparable to what has been obtained with the iterative correction method and may indicate, despite its lower precision, a more computationally efficient as well as robust method of estimating axial strain.

The new concept described in this paper is based on the direct estimation of tissue strain from the relative frequency shift in the power spectrum. The estimator hereby presented, namely the centroid shift estimator, measures the shift by calculating the relative centroid shift resulting from the applied compression. This estimator has three major characteristics: it is a) direct and b) spectral, i.e., operates in the frequency domain. The direct strain estimation assures that no noise is added through the use of gradient operators, as is the case in time-delay based elastographic techniques. The spectral characteristic makes this method more robust since it is phase independent and, therefore, suffers less from motion-induced decorrelation noise. Another estimator that is theoretically shown to provide a direct measure of strain is the resulting relative change of bandwidth in the power spectrum. The bandwidth parameter can also be used to eliminate the bias corrupting the centroid estimator.

In order to study the performance of the centroid estimator, we used a I-D simulation model that allowed the scatterers to move solely in the axial direction. Preliminary results obtained with these I-D simulations are used to demonstrate the robustness of the proposed method. Strain estimates as high as 10% are produced at a reasonably high signal-to-noise ratio while the standard crosscorrelation-based elastographic method practically failed beyond the levels of 2%. The 1-D example was preferred (to 2-D or 3-D simulations) so that the performance of the method could be characterized independent of noise due to 2-D or 3-D motion. If the 2-D or 3-D scenario were used, the estimators would fail at lower strains, but the spectral centroid estimator, not being sensitive to phase changes, would still be more robust than the RF crosscorrelation estimators. In fact, phantom experiments were used to show that the centroid estimator could generate quality elastograms at applied strains as high as 3% while the cross-correlation based elastograms are extremely noisy. Furthermore, simulation results showed that the spectral centroid shift method provided a jitter insensitive method of estimating the strain. Therefore, spectral strain estimation may be particularly useful for obtaining good elastograms in noisy jitter environments produced by unpredictable tissue and/or system motion. This may constitute a major advantage, since elastography might be practiced using the same clinical guidelines employed by ultrasound: i.e., using a hand-held transducer. In addition, the jitter resistance of the centroid estimator could make it suitable for use in intravascular elastography in vivo, a task that has not been demonstrated as feasible using cross-correlation techniques. Future investigations will involve theoretical study of the performance of spectral (i.e., frequency and shift and bandwidth) strain estimators as well as experimental verification of their jitter insensitivity.

The foregoing disclosure and description of the invention are illustrative and explanatory. Various changes in the size, shape, and materials, as well as in the details of the illustrative construction may be made without departing from the spirit of the invention.

What is claimed:

1. A method for measuring strain in a target body comprising:
   a. acoustically coupling a transducer to the outer surface of a target body such that the path of a beam emitted from the transducer defines a transducer axis;
   b. emitting first a pulse of ultrasound energy into the target body along the transducer axis;
   c. receiving a first reflected signal with the transducer;
   d. storing the first reflected signal;
   e. allowing the target to change dimensions along the axis defined by the transducer;
   f. emitting a second pulse of ultrasound energy into the target body along the transducer axis;
   g. receiving a second reflected signal with the transducer;
   h. storing the second reflected signal;
   i. selecting a portion of the first and second reflected signals;
   j. computing the frequency spectrum of each of the selected portions of the first and second selected signals;
   k. computing the shift between the computed spectra; and
   l. normalizing the computed shift to one of the computed spectra.

2. The method of claim 1 wherein allowing the target to change dimensions is accomplished by applying a compressive force to the target.

3. The method of claim 1 wherein allowing the target to change dimensions is accomplished by reducing a compressive force to the target.

4. A method of claim 1 wherein computing the frequency spectrum of each of the selection portions of the first and second selected signals is accomplished using Fourier analysis.

* * * * *

UNITED STATES PATENT AND TRADEMARK OFFICE
CERTIFICATE OF CORRECTION

PATENT NO. : 6,494,834 B2
APPLICATION NO. : 09/810958
DATED : December 17, 2002
INVENTOR(S) : Elisa Konofagou and Jonathan Ophir It is certified that error appears in the above-identified patent and that said Letters Patent is hereby corrected as shown below:

Column 1,
Line 12, insert -- GOVERNMENT RIGHTS
This invention was made with government support under contract number
PO1 CA064597 awarded by the National Institutes of Health. The government has certain rights in the invention. --

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

PATENT NO. : 6,494,834 B2
APPLICATION NO. : 09/810958
DATED : December 17, 2002
INVENTOR(S) : Elisa Konofagou and Jonathan Ophir It is certified that error appears in the above-identified patent and that said Letters Patent is hereby corrected as shown below:

In the Specification

In Column 1, after the portion stating "This application claims the benefit of U.S. Provisional Application No. 60/190,718, filed on Mar. 17, 2000" and before the portion entitled BACKGROUND, insert the following Government Support Clause:
--This invention was made with government support under CA064597 awarded by National Institutes of Health. The government has certain rights in the invention.--

This certificate supersedes the Certificate of Correction issued October 6, 2009.

Signed and Sealed this
Eighth Day of October, 2024

Katherine Kelly Vidal
*Director of the United States Patent and Trademark Office*